(12) United States Patent
Beasley et al.

(10) Patent No.: US 8,303,940 B2
(45) Date of Patent: Nov. 6, 2012

(54) PHOTOSTABILIZATION OF OCTYL TRIAZONE

(75) Inventors: Donathan G. Beasley, Memphis, TN (US); Thomas A. Meyer, Germantown, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 0 days.

(21) Appl. No.: 11/862,747

(22) Filed: Sep. 27, 2007

(65) Prior Publication Data

US 2009/0087394 A1 Apr. 2, 2009

(51) Int. Cl.
*A61K 8/00* (2006.01)
(52) U.S. Cl. .................................................. 424/59
(58) Field of Classification Search ................... None
See application file for complete search history.

(56) References Cited

U.S. PATENT DOCUMENTS 6,440,402 B1 * 8/2002 Gonzalez et al. ............... 424/59
2008/0131381 A1 6/2008 Chaudhuri et al.

FOREIGN PATENT DOCUMENTS

| EP | 1 591 099 A2 | 11/2005 |
| EP | 1 649 900 A2 | 4/2006 |
| WO | 2007/128744 A2 | 11/2007 |

OTHER PUBLICATIONS

Chaudhuri et al., Design of a Photostabilizer Having Built-in Antioxidant Functionality and Its Utility in Obtaining Broad-spectrum Sunscreen Formulations, Photochemistry and Photobiology, 82:823-828.*
Chaudhuri et al., Design of a Photostabilizer Having Built-in Antioxidant Functionality and Its Utility in Obtaining Broad-spectrum Sunscreen Formulations, Photochemistry and Photobiology, 82:823-828, 2006.*
Maier et al. Photodermatol Photoimmunol Photomed 21: 84-92 (2005).*
Diffey et al., Eur J Dermatol 7: 226-8 (1997).*
Serpone et al., Photochem Photobio Sci 1: 970-981 (2002).*
Pfluecker, et al., Cosmetics and Toiletries Manufacture Worldwide May 31, 2006.*
Sayre et al., Allured's Cosmetics and Toiletries magazine vol. 114(5) (1999).*
Bonda, Craig; "Research Pathways to Photostable Sunscreens"; Cosmetics & Toiletries; 123(22):1,49-60 (Feb. 2008).
"The Photostability of Organic Sunscreen Additives: A Review," Craig A. Bonda, Table 17.3 on p. 337 and table 17.5 on p. 338, in Sunscreens, Regulations and Commercial Development, Third edition.

* cited by examiner

*Primary Examiner* — Robert T. Crow
*Assistant Examiner* — Thor Nielsen
(74) *Attorney, Agent, or Firm* — Dianne Pecoraro; Catherine D. Fitch

(57) ABSTRACT

Methods and compositions useful in enhancing protection from UV radiation, the compositions containing octyl triazone and diethylthexyl syringylidene malonate in an amount effective to photostabilize octyl triazone.

36 Claims, No Drawings

PHOTOSTABILIZATION OF OCTYL TRIAZONE

BACKGROUND OF THE INVENTION

When applied topically, sunscreen compositions impart a film that protects skin against the damaging effects of exposure to sun's ultraviolet radiation (UVR). Sunscreen actives work on skin's surface by absorbing UVR before it can interact with and damage skin. For maximum skin protection, sunscreen actives must be photostable, maintaining their ability to absorb UVR throughout periods of sun exposure. When sunscreen actives lose their ability to absorb UVR, they become less photoprotective, as more UVR passes thru the protective film to reach underlying skin.

Several sunscreen actives display signs of photoinstability, with perhaps the best-known example being avobenzone, a UVA sunscreen active. Avobenzone's potential to photodegrade represents a major disadvantage in formulation of sunscreen compositions that provide sustained UVA protection during periods of sun exposure. However, in recent years, avobenzone's disadvantage has been overcome by adopting formulation strategies that minimize photodegradation of avobenzone. These strategies include omission of ingredients that are photochemically incompatible with avobenzone (for example, octinoxate) or inclusion of ingredients that help stabilize avobenzone in the presence of UVR. Thus, it is now possible to formulate sunscreen compositions containing avobenzone that provide effective, durable UVA protection to skin over the entire time course of sun exposure.

As a UVB sunscreen active, octyl triazone also shows signs of photoinstability when irradiated with UVR. We have now discovered, surprisingly, that addition of diethylhexyl syringylidene malonate to sunscreen compositions containing octyl triazone significantly enhances octyl triazone's stability during UVR exposure.

SUMMARY OF THE INVENTION

The invention provides a method for stabilizing octyl triazone in a composition from degradation due to exposure to UV radiation, the method comprising the step of incorporating into the composition a photostabilization effective amount of diethylhexyl syrigylidene malonate.

The invention further provides a method for enhancing the UV radiation protective effect of a composition comprising octyl triazone, the method comprising incorporating into the composition a photostabilization effective amount of diethylhexyl syrigylidene malonate thereby enhancing UV radiation protection of the composition.

The invention also provides a composition comprising one or more sunscreen active agents wherein at least one sunscreen active agent is octyl triazone, the composition further comprising a photostabilization effective amount of diethylhexyl syrigylidene malonate.

The invention further provides a method for protecting a subject from damaging UV radiation which comprises applying to the subject a composition comprising one or more sunscreen active agents, wherein at least one sunscreen active agent is octyl triazone, the composition further comprising a photostabilization effective amount of diethylhexyl syrigylidene malonate.

These and other objectives are further described and claimed herein. All patents and references cited herein are hereby incorporated in their entirety into the present specification.

DETAILED DESCRIPTION OF THE INVENTION

Unless otherwise defined herein, names given to chemical substances herein generally are either accepted chemical names, or are trade organization or regulatory agency approved names such as CTFA Adopted Names as listed in J. A. Wenninger et al., Eds., CTFA International Cosmetic Ingredient Dictionary, Eighth Ed., The Cosmetic, Toiletry and Fragrance Association, Washington, D.C., 2000.

Octyl triazone is a UV-B absorber (also known as (4,6-trianilino-p-(carbo-2'-ethylhexyl-1'-oxy)-1,3,5-triazine; Tradename: Uvinul® T 150 (BASF; New Jersey USA)) and has the structure:

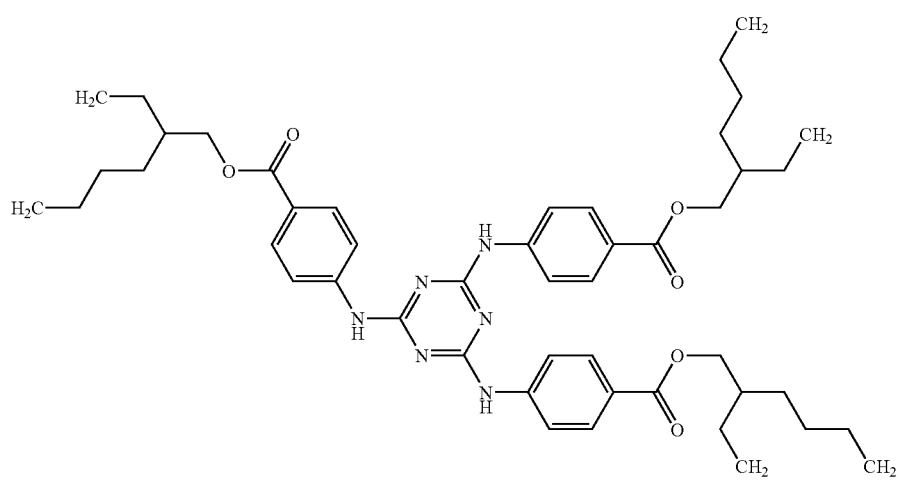

Diethylhexyl syrigylidene malonate is also known as 2-(4-Hydroxy-3,5-dimethoxybenzylidene)-malonic acid bis-(2-ethylhexyl)ester ("DESM"; Tradename Oxynex® ST, (Merck KGaA, Darmstadt, Germany)) and has the structure:

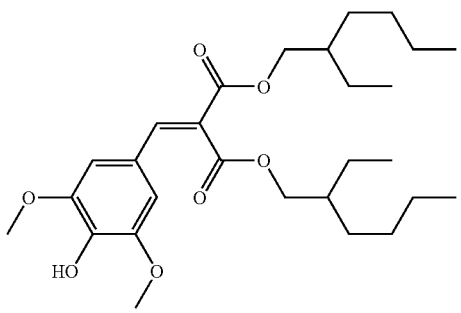

Methods of making compositions containing octyl triazone are known in the art. See, e.g., U.S. Pat. Nos. 5,968,481, 6,096,294 and 6,776,980. Methods of making compositions containing DESM are also known. See, e.g., U.S. Pat. Nos. 7,166,273 and 7,150,876. However, prior to the subject invention, it was not known, nor was it obvious that the UV-B absorber octyl triazone would be photostabilized in compositions by the addition of DESM.

In example embodiments of the methods and compositions of the invention, the photostabilization effective amount of diethylhexyl syrigylidene malonate can be an amount from about 0.5% to about 5% by weight. In additional example embodiments of the methods and compositions of the invention, the photostabilization effective amount of diethylhexyl syrigylidene malonate can be an amount from about 1.5% to about 3% by weight. In additional example embodiments of the methods and compositions of the invention, the photostabilization effective amount of diethylhexyl syrigylidene malonate can be an amount of about 2% by weight. In additional example embodiments of the methods and compositions of the invention, the photostabilization effective amount of diethylhexyl syrigylidene malonate can be an amount of about 4% by weight.

In example embodiments of the methods and compositions of the invention, the composition may comprise from about 0.5% to about 5% octyl triazone by weight. In additional example embodiments of the methods and compositions of the invention, the composition may comprise from about 1% to about 2% octyl triazone by weight. In additional example embodiments of the methods and compositions of the invention, the composition may comprise about 1% octyl triazone by weight.

The term "percent by weight" as used herein means the percent by weight of the ingredient per weight of the overall formulation.

The compositions prepared according to this invention may comprise emulsions, including, e.g., oil-in-water emulsions or water-in-oil emulsions, or aqueous solutions including, e.g., aqueous alcoholic or alcoholic vehicles.

Products that may be formulated to contain octyl triazone as a sunscreen active include moisturizers, cleansers, conditioners, shampoo, body wash, styling gel/lotion, eye cream and eye liner, blush, mascara, foundation, nail polish, polish remover, eye shadow, lipstick, lip gloss, lip liners, lip balms, makeup remover, nail treatment, foot care compositions, acne treatment, redness/rosacea treatment, varicose/spider vein treatment, anti-aging compositions, sunscreens, sunless tanning compositions, after-sun compositions, concealers, hair color and bleaching compositions, skin fading/lighteners, body firming lotion, shaving cream, after shave, relaxer, antiperspirants and deodorants, exfoliants, scrubs, liquid hand soap, bubble bath, pain and wound treatment compositions, insect repellant, anti-itch and rash cream, styling mousse and foams, bath oils and salts, toothpaste, perfume, glitter, lubricants, body powder, body oil, body spray, baby lotion, diaper cream, baby soap, baby shampoo, baby oil, baby wipes, hair-loss treatment, hair spray, cuticle treatment, dandruff/scalp treatment, depilatory, hair growth inhibitors, hair removal waxes, personal cleansing, cologne, oil controller, hand sanitizer, mouthwash, tooth whitening, eye drops, and artificial tears compositions. Any formulations of these types are contemplated to be within the scope of this invention.

The compositions of the present invention may contain a wide range of additional, optional components which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, waterproofing agents, and viscosity increasing agents (aqueous and nonaqueous).

In the practice of the invention, the composition may contain one or more additional sunscreen active agents. For purposes of the present invention, a "sunscreen active agent" or "sunscreen active" shall include all of those materials, singly or in combination, that are regarded as acceptable for use as active sunscreening ingredients based on their ability to absorb UV radiation. Such compounds are generally described as being UV-A, UV-B, or UV-A/UV-B active agents. As used herein sunscreen active ingredient include all hydrophilic, lipophilic or particulate (e.g., $TiO_2$, ZnO or Tinosorb M) sunscreen actives. Approval by a regulatory agency is generally required for inclusion of active agents in formulations intended for human use. Those active agents which have been or are currently approved for sunscreen use in the United States include organic and inorganic substances including, without limitation, para-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the US but are allowed in formulations sold outside of the US include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved sunscreens is currently expanding, those of ordinary skill will recognize that the invention is not limited to sunscreen active agents currently approved for human use but is readily applicable to those sunscreen active agents that may be allowed in the future.

As used herein, the term "sunless-tanning" or "self-tanning compositions" refer to compositions which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self tanning agent, effective amounts of a composition coloring agent and a cosmetically acceptable carrier adapted for topical application to human skin. The self tanning agents can also include those compositions generally accepted in the art for application to human skin, and which, when so applied, react therein with amino acids so as to form pigmented products. Such reactions give the skin a brown appearance similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self tanning agents are the alpha-hydroxy aldehydes and ketones. Most preferably, the self tanning agent is dihydroxyacetone ("DHA"). Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

The compositions of the invention can further comprise skin protectant active agents. Suitable examples include (with preferred weight percent ranges), Allantoin (0.5 to 2 percent); Aluminum hydroxide gel (0.15 to 5 percent); Calamine (1 to 25 percent); Cocoa butter (greater than 50); Cod liver oil (5 to 14 percent); Colloidal oatmeal; Dimethicone (1 to 30 percent), Glycerin (20 to 45 percent); Hard fat (greater than 50); Kaolin (4 to 20 percent); Lanolin (12.5 to 50 percent); Mineral oil (greater than 50 percent); Petrolatum (greater than 30 percent); Sodium bicarbonate; Topical starch (10 to 98 percent), White petrolatum (greater than 30 percent); Zinc acetate (0.1 to 2 percent); Zinc carbonate (0.2 to 2 percent); and Zinc oxide (1 to 25 percent).

The compositions of the invention may further include insect repelling components. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Suitable emulsifiers or surfactants include pharmaceutically acceptable, non-toxic, non-ionic, anionic and cationic surfactants. Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, and the like. Examples of suitable anionic surfactants are soaps including alkali soaps, such as sodium, potassium and ammonium salts of aliphatic carboxylic acids, usually fatty acids, such as sodium stearate. Organic amine soaps include organic amine salts of aliphatic carboxylic acids, usually fatty acids, such as triethanolamine stearate. Metallic soaps include salts of polyvalent metals and aliphatic carboxylic acids, usually fatty acids, such as aluminium stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sultonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sulfonate such as aryl napthalene with alkyl substitutes. Examples of suitable cationic surfactants include amine salts such as octadecyl ammonium chloride, quartemary ammonium compounds such as benzalkonium chloride.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin cross-linked glyceryl starch of the type that is disclosed in U.S. Pat. No. 6,488,916.

It may be advantageous to incorporate additional thickening agents, such as, for instance, various Carbopols available from Noveon Co. Particularly preferred are those agents which would not disrupt the emulsion in the formulation of the final product, such as non-ionic thickening agents. The selection of additional thickening agents is well within the skill of one in the art.

An "antioxidant" is a natural or synthetic substance added to the sunscreen to protect from or delay its deterioration due to the action of oxygen in the air (oxidation). They may also reduce oxidation reactions in skin tissue. Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), green tea extract, uric acid, cysteine, pyruvate, nordihydroguaiaretic acid, Vitamin A, Vitamin E and Vitamin C and their derivatives. One or more antioxidants can optionally be included in the sunscreen composition in an amount ranging from about 0.001 to about 5 weight percent, preferably about 0.01 to about 0.5 percent.

"Chelating agents" are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, or combinations of any of these.

"Fragrances" are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 5 weight percent, preferably about 0.01 to about 0.5 percent by weight. Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

The invention will be further described by means of the following examples, which are not intended to limit the invention, as defined by the appended claims, in any manner.

EXAMPLE 1

To demonstrate the ability of diethylhexyl syringylidene malonate ("DESM") to enhance octyl triazone's photostability, sunscreen emulsion compositions containing 1% octyl triazone were formulated with different levels of DESM (0, 2, or 4%) (Table 1). The emulsion compositions were then spread as a film on a surface and then irradiated with UVR for varying lengths of time. As explained in more detail below, films were prepared on Transpore Tape, allowed to air dry and then irradiated continuously in the time mode using an Optometrics SPF-290S SPF Analyzer System. The stability of octyl triazone during continuous UVR exposure was monitored by noting the loss in absorption at 315 nm due to octyl triazone.

TABLE 1

Sunscreen emulsions containing 1% octyl triazone and varying levels of DSM.[a]

| Ingredient | Emulsion A | Emulsion B | Emulsion C |
|---|---|---|---|
| Part A | | | |
| Oxynex ST | — | 2.00000 | 4.00000 |
| Uvinul T 150 | 1.00000 | 1.00000 | 1.00000 |
| Spectrasolv 10 | 11.00000 | 9.00000 | 7.00000 |
| D.C. 200 Fluid 350 CS | 0.40000 | 0.40000 | 0.40000 |
| Propylparaben, NF | 0.10000 | 0.10000 | 0.10000 |
| PVP/Eicosene Copolymer | 1.00000 | 1.00000 | 1.00000 |
| Crill 6 | 5.00000 | 5.00000 | 5.00000 |
| Cremophor GS-32 | 2.00000 | 2.00000 | 2.00000 |
| Stearic Acid, NF Trip Pressed | 2.00000 | 2.00000 | 2.00000 |
| Polyanhydride Resin PA-18 | 2.00000 | 2.00000 | 2.00000 |
| Methylparaben, NF | 0.20000 | 0.20000 | 0.20000 |
| Part B | | | |
| USP Purified Water | 56.96500 | 56.96500 | 56.96500 |
| Sorbitol Solution 70%, USP | 5.00000 | 5.00000 | 5.00000 |
| Disodium EDTA | 0.01000 | 0.01000 | 0.01000 |
| Carbopol Ultrez 10 | 0.07500 | 0.07500 | 0.07500 |
| Part C | | | |
| USP Purified Water | 10.00000 | 10.00000 | 10.00000 |
| Triethanolamine, 99% NF | 2.25000 | 2.25000 | 2.25000 |
| Part D | | | |
| Benzyl Alcohol, NF | 1.00000 | 1.00000 | 1.00000 |
| TOTAL | 100.00000 | 100.00000 | 100.00000 |

[a]Amounts recited in percent by weight.

The emulsions were prepared by mixing the ingredients of Part A in a beaker and heating to 175-185° F. until the mixture appears uniform. In a separate container large enough to hold the entire batch, the carbopol of Part B is added to the water with stirring and mixed until it is clear and lump-free. While mixing, the remaining ingredients of part B then are added to the container. After all the ingredients of Part B have been added to the container, Part A is added slowly to the container containing the ingredients of Part B with constant mixing, followed by addition of the mixture of Part C ingredients. The emulsion is then stirred as it cools to room temperature, at which point Part D is added and well-mixed into the emulsion Photostability of octyl triazone in each formulation was assessed by monitoring the loss in absorbance at 315 nm during continuous exposure of lotion films to ultraviolet radiation. Films of each emulsion were prepared on Transpore Tape (3M Health Care, St. Paul, Minn. 55144) by applying a sufficient amount of emulsion to yield an application density of 2 mg/cm$^2$. Each emulsion was rubbed onto the surface of the tape using a finger covered with a fingercot. After application, the Transpore Tape was air-dried for 20 minutes. An untreated piece of Transpore Tape served as a reference and a blank during testing.

Photostability was assessed using an SPF 290S Analyzer (Optometrics LLC, Ayer, Mass. 01432) in the time course mode according to the manufacturer's operating instructions. In the time-course mode, films were irradiated continuously over 11 minutes and measurements were recorded at 1 minute intervals as monochromatic protection factor (MPF). The MPF values at 315 nm were converted subsequently to absorbance (ABS) using the following equation:

$$ABS = \log(MPF)$$

These absorbance values at each time point were then used to calculate the percent absorbance due to octyl triazone remaining (see Table 2) over the irradiation period using the following equation:

$$\% ABS = \frac{\text{Observed } ABS}{\text{Initial } ABS} \times 100\%$$

where initial ABS is equal to the absorbance at 315 nm at time=0 and observed ABS is absorbance at each time point.

TABLE 2

| Time (min) | Emulsion A 0% DSM | Emulsion B 2% DSM | Emulsion C 4% DSM |
| --- | --- | --- | --- |
| 0 | 100% | 100% | 100% |
| 1 | 89% | 97% | 95% |
| 2 | 85% | 98% | 95% |
| 3 | 82% | 97% | 95% |
| 4 | 79% | 97% | 95% |
| 5 | 76% | 97% | 95% |
| 6 | 73% | 97% | 94% |
| 7 | 71% | 96% | 94% |
| 8 | 69% | 96% | 94% |
| 9 | 66% | 95% | 94% |
| 10 | 64% | 95% | 93% |
| 11 | 62% | 94% | 92% |

The data in Table 2 demonstrate DESM's ability to enhance octyl triazone's photostability. Table 2 shows clearly that octyl triazone in the absence of DSM undergoes degradation throughout the time course of irradiation. In contrast, addition of DESM at 2% or 4% significantly enhances octyl triazone's photostability. For example, after irradiation for 11 minutes, octyl triazone degraded by about 38% in the control emulsion compared with only about 8% in the emulsions containing either 2% or 4% DESM. Thus, these data demonstrate that DESM significantly enhances octyl triazone's photostability in thin films when irradiated with UVR. Improving photostability with DESM improves the photoprotective power of octyl triazone on skin throughout entire exposures to UVR.

What is claimed is:

1. A method for stabilizing octyl triazone in a composition from degradation due to exposure to UV radiation, the method comprising the step of incorporating into the composition an amount of diethylhexyl syringylidene malonate effective to photostabilize octyl triazone.

2. The method of claim 1 wherein the photostabilization effective amount of diethylhexyl syringylidene malonate is from about 0.5% to about 5% by weight.

3. The method of claim 1 wherein the photostabilization effective amount of diethylhexyl syringylidene malonate is from about 1.5% to about 3% by weight.

4. The method of claim 1 wherein the photostabilization effective amount of diethylhexyl syringylidene malonate is about 2% by weight.

5. The method of claim 1 wherein the photostabilization effective amount of diethylhexyl syringylidene malonate is about 4% by weight.

6. The method of claim 1 wherein the composition comprises from about 0.5% to about 5% octyl triazone by weight.

7. The method of claim 1 wherein the composition comprises from about 1% to about 2% octyl triazone by weight.

8. The method of claim 1 wherein the composition comprises about 1% octyl triazone by weight.

9. A method for enhancing the UV radiation protective effect of a composition comprising octyl triazone, the method comprising incorporating into the composition an amount of diethylhexyl syringylidene malonate effective to photostabilize octyl triazone, thereby enhancing UV radiation protection of the composition.

10. The method of claim 9 wherein the photostabilization effective amount of diethylhexyl syringylidene malonate is from about 0.5% to about 5% by weight.

11. The method of claim 9 wherein the photostabilization effective amount of diethylhexyl syringylidene malonate is from about 1.5% to about 3% by weight.

12. The method of claim 9 wherein the photostabilization effective amount of diethylhexyl syringylidene malonate is about 2% by weight.

13. The method of claim 9 wherein the photostabilization effective amount of diethylhexyl syringylidene malonate is about 4% by weight.

14. The method of claim 9 wherein the composition comprises from about 0.5% to about 5% octyl triazone by weight.

15. The method of claim 9 wherein the composition comprises from about 1% to about 2% octyl triazone by weight.

16. The method of claim 9 wherein the composition comprises about 1% octyl triazone by weight.

17. A composition comprising one or more sunscreen active agents wherein at least one sunscreen active agent is octyl triazone, the composition further comprising an amount of diethylhexyl syringylidene malonate effective to photostabilize octyl triazone.

18. The composition of claim 17 wherein the photostabilization effective amount of diethylhexyl syringylidene malonate is from about 0.5% to about 5% by weight.

19. The composition of claim 17 wherein the photostabilization effective amount of diethylhexyl syringylidene malonate is from about 1.5% to about 3% by weight.

20. The composition of claim 17 wherein the photostabilization effective amount of diethylhexyl syringylidene malonate is about 2% by weight.

21. The composition of claim 17 wherein the photostabilization effective amount of diethylhexyl syringylidene malonate is about 4% by weight.

22. The composition of claim 17 wherein the composition comprises from about 0.5% to about 5% octyl triazone by weight.

23. The composition of claim 17 wherein the composition comprises from about 1% to about 2% octyl triazone by weight.

24. The composition of claim 17 wherein the composition comprises about 1% octyl triazone by weight.

25. The composition of claim 17, wherein the composition is a sunscreen composition.

26. The composition of claim 17 wherein the composition is a self tanning composition.

27. The composition of claim 25 wherein the composition comprises one or more additional sunscreen active agents chosen from the group consisting of para-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate.

28. A method for protecting a subject from damaging UV radiation which comprises applying to the subject a composition comprising one or more sunscreen active agents, wherein at least one sunscreen active agent is octyl triazone, the composition further comprising an amount of diethylhexyl syringylidene malonate effective to photostabilize octyl triazone.

29. The method of claim 28 wherein the photostabilization effective amount of diethylhexyl syringylidene malonate is from about 0.5% to about 5% by weight.

30. The method of claim 28 wherein the photostabilization effective amount of diethylhexyl syringylidene malonate is from about 1.5% to about 3% by weight.

31. The method of claim 28 wherein the photostabilization effective amount of diethylhexyl syringylidene malonate is about 2% by weight.

32. The method of claim 28 wherein the photostabilization effective amount of diethylhexyl syringylidene malonate is about 4% by weight.

33. The method of claim 28 wherein the composition comprises from about 0.5% to about 5% octyl triazone by weight.

34. The method of claim 28 wherein the composition comprises from about 1% to about 2% octyl triazone by weight.

35. The method of claim 28 wherein the composition comprises about 1% octyl triazone by weight.

36. The method of claim 28 wherein the composition comprises one or more additional sunscreen active agents chosen from the group consisting of para-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate.

\* \* \* \* \*